(12) United States Patent
Miyaji et al.

(10) Patent No.: US 7,960,425 B2
(45) Date of Patent: Jun. 14, 2011

(54) PYRAZOLE COMPOUNDS AND THROMBOPOIETIN RECEPTOR ACTIVATORS

(75) Inventors: Katsuaki Miyaji, Funabashi (JP); Yutaka Hirokawa, Funabashi (JP); Masato Horikawa, Minamisaitama-gun (JP); Norihisa Ishiwata, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 724 days.

(21) Appl. No.: 11/995,070

(22) PCT Filed: Jul. 19, 2006

(86) PCT No.: PCT/JP2006/314713
§ 371 (c)(1),
(2), (4) Date: Jan. 8, 2008

(87) PCT Pub. No.: WO2007/011056
PCT Pub. Date: Jan. 25, 2007

(65) Prior Publication Data
US 2009/0131676 A1 May 21, 2009

(30) Foreign Application Priority Data

Jul. 20, 2005 (JP) ................. 2005-210646
Jul. 20, 2005 (JP) ................. 2005-210647
May 26, 2006 (JP) ................. 2006-146116

(51) Int. Cl.
*A61K 31/4155* (2006.01)
*C07D 231/18* (2006.01)
(52) U.S. Cl. .................... 514/406; 548/365.7
(58) Field of Classification Search .............. 514/406; 548/365.7
See application file for complete search history.

(56) References Cited

U.S. PATENT DOCUMENTS

| | | |
|---|---|---|
| 2003/0195231 A1 | 10/2003 | Takemoto et al. |
| 2004/0063764 A1 | 4/2004 | Takemoto et al. |
| 2004/0077697 A1 | 4/2004 | Koshio et al. |
| 2004/0082626 A1 | 4/2004 | Takemoto et al. |
| 2005/0153977 A1 | 7/2005 | Sugasawa et al. |

FOREIGN PATENT DOCUMENTS

| EP | 1 207 155 A1 | 5/2002 |
|---|---|---|
| JP | 10-72492 | 3/1998 |
| JP | 11-1477 | 1/1999 |
| JP | 11-152276 | 6/1999 |
| JP | 2001-97948 | 4/2001 |
| JP | 2003/238565 | 8/2003 |
| WO | WO 96/40189 | 12/1996 |
| WO | WO 96/40750 | 12/1996 |
| WO | WO 98/25965 | 6/1998 |
| WO | WO 99/11262 | 3/1999 |
| WO | WO 00/35446 | 6/2000 |
| WO | WO 00/66112 | 11/2000 |
| WO | WO 01/07423 A1 | 2/2001 |
| WO | WO 01/17349 A1 | 3/2001 |
| WO | WO 01/21180 A1 | 3/2001 |
| WO | WO 01/34585 A1 | 5/2001 |
| WO | WO 01/39773 A1 | 6/2001 |
| WO | WO 01/53267 A1 | 7/2001 |
| WO | WO 01/89457 A2 | 11/2001 |
| WO | WO 02/49413 A2 | 6/2002 |
| WO | WO 02/059099 A1 | 8/2002 |
| WO | WO 02/59100 A1 | 8/2002 |
| WO | WO 02/062775 A1 | 8/2002 |
| WO | WO 02/085343 A1 | 10/2002 |
| WO | WO 03/062233 A1 | 7/2003 |
| WO | 2004/033433 | 4/2004 |
| WO | WO 2004/033433 A1 | 4/2004 |
| WO | 2004/108683 | 12/2004 |
| WO | WO 2004/108683 A1 | 12/2004 |
| WO | 2006/064957 | 6/2006 |
| WO | WO 2006/064957 A1 | 6/2006 |

OTHER PUBLICATIONS

U.S. Appl. No. 12/492,435, filed Jun. 26, 2009, Owada, et al.
U.S. Appl. No. 12/303,436, filed Dec. 4, 2008, Miyaji, et al.
Jose E. Cardier, "Effects of Megakaryocyte Growth and Development Factor (Thrombopoietin) on Liver Endothelial Cells in Vitro", Microvascular Research, vol. 58, 1999, pp. 108-113.
Maria Felice Brizzi, et al., "Thrombopoietin Stimulates Endothelial Cell Motility and Neoangiogenesis by a Platelet-Activating Factor-Dependent Mechanism", Circulation Research, vol. 84, 1999, pp. 785-796.
"Blood", Journal of the American Society of Hematology, vol. 98, No. 11, Nov. 16, 2001, pp. 71a-72a and a cover page.

*Primary Examiner* — Taofiq A Solola
(74) *Attorney, Agent, or Firm* — Oblon, Spivak, McClelland, Maier & Neustadt, L.L.P.

(57) ABSTRACT

A compound represented by the formula (I) (wherein $R^1$, $R^2$, $R^3$ and $R^4$ are as defined in the description), a tautomer, prodrug or pharmaceutically acceptable salt of the compound or a solvate thereof.

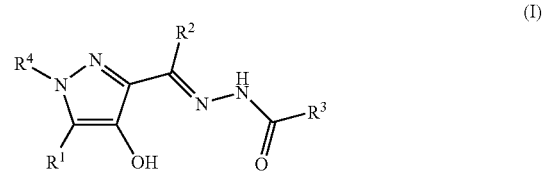

(I)

23 Claims, No Drawings

PYRAZOLE COMPOUNDS AND THROMBOPOIETIN RECEPTOR ACTIVATORS

BACKGROUND OF THE INVENTION

1. Technical Field

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

2. Background Art

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 26).

1) Applications filed by Hokuriku Seiyaku Co., Ltd. relating to 1,4-benzodiazepine derivatives (patent documents 5 and 6)
2) International Laid-open Patent Applications filed by Shionogi & Co., Ltd. (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application filed by Roche Diagnostics GMBH (patent document 21)
6) International Laid-open Patent Applications filed by Yamanouchi Pharmaceutical Co., Ltd. (patent document 22 and 23)
7) Japanese Laid-open Patent Application filed by Japan Tabacco Inc. (patent document 24)
8) International Laid-open Patent Application filed by Nissan Chemical Industries, Ltd. (patent documents 25 and 26)

Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO01/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Patent document 25 WO04/033433
Patent document 26 WO04/108683
Non-patent document 1 Microvasc. Res., 1999: 58, p. 108-113
Non-patent document 2 Circ. Res., 1999: 84, p. 785-796
Non-patent document 3 Blood 2001:98, p. 71a-72a

DISCLOSURE OF THE INVENTION

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (I):

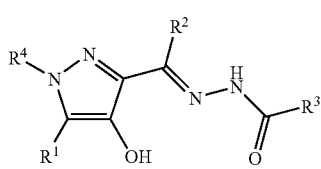

wherein $R^1$ is a phenyl group (the phenyl group may be substituted with one or more $C_{1-6}$ alkyl groups, one or more $C_{1-3}$ alkyl groups (the $C_{1-3}$ alkyl groups are substituted with one or more halogen atoms) or one or more halogen atoms), $R^2$ is a hydrogen atom or a $C_{1-3}$ alkyl group (the $C_{1-3}$ alkyl group may be substituted with one or more halogen atoms), $R^3$ is a thienyl group (the thienyl group is substituted with $(C=O)NR^5R^6$ (wherein $R^5$ is a hydrogen atom or a $C_{1-3}$ alkyl group (the $C_{1-3}$ alkyl group may be substituted with one or more halogen atoms), and $R^6$ is a $C_{1-6}$ alkyl group (the $C_{1-6}$ alkyl group may be substituted with one or more halogen atoms, one or more hydroxyl groups, one or more $C_{1-3}$ alkoxy groups (the $C_{1-3}$ alkoxy groups may be substituted with one or more halogen atoms), one or more phenyl groups, one or more thienyl groups, one or more furyl groups or one or more pyridyl groups))), and $R^4$ is a $C_{1-3}$ alkyl group (the $C_{1-3}$ alkyl group may be substituted with one or more halogen atoms), a tautomer, prodrug or pharmaceutically acceptable salt of the compound or a solvate thereof.
2. The compound according to 1, wherein $R^2$ and $R^4$ are methyl groups, a tautomer, prodrug or pharmaceutically acceptable salt of the compound or a solvate thereof.
3. The compound according to 2, wherein $R^1$ is a 3,4-dimethylphenyl group, a 4-trifluoromethylphenyl group or a 3,4-dichlorophenyl group, a tautomer, prodrug or pharmaceutically acceptable salt of the compound or a solvate thereof.
4. The compound according to 3, wherein $R^3$ is represented by the formula (II):

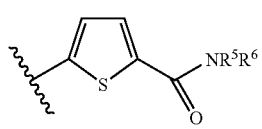

(wherein $R^5$ is a hydrogen atom or a $C_{1-3}$ alkyl group, and $R^6$ is a $C_{1-3}$ alkyl group (the $C_{1-3}$ alkyl group is substituted with a 2-pyridyl group)), a tautomer, prodrug or pharmaceutically acceptable salt of the compound or a solvate thereof.
5. The compound according to 3, wherein $R^3$ is represented by the formula (II):

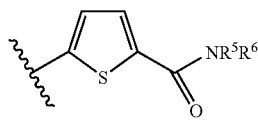

(wherein $R^5$ is a $C_{1-3}$ alkyl group, and $R^6$ is a $C_{1-6}$ alkyl group), a tautomer, prodrug or pharmaceutically acceptable salt of the compound or a solvate thereof.

6. The compound according to 3, wherein $R^3$ is represented by the formula (II):

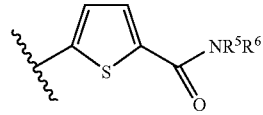

(wherein $R^5$ is a hydrogen atom or a $C_{1-3}$ alkyl group, and $R^6$ is a $C_{1-3}$ alkyl group (the $C_{1-3}$ alkyl group is substituted with a 4-pyridyl group or a $C_{1-3}$ alkoxy group)), a tautomer, prodrug or pharmaceutically acceptable salt of the compound or a solvate thereof.
7. The compound according to 3, wherein $R^3$ is represented by the formula (II):

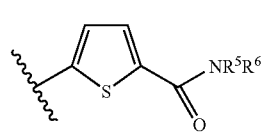

(wherein $R^5$ is a hydrogen atom, and $R^6$ is a $C_{1-3}$ alkyl group), a tautomer, prodrug or pharmaceutically acceptable salt of the compound or a solvate thereof.
8. The compound according to any one of 4 to 7, wherein $R^1$ is a 4-trifluoromethylphenyl group, a tautomer, prodrug or pharmaceutically acceptable salt of the compound or a solvate thereof.
9. The compound according to any one of 4 to 7, wherein $R^1$ is a 3,4-dichlorophenyl group, a tautomer, prodrug or pharmaceutically acceptable salt of the compound or a solvate thereof.
10. The compound according to any one of 4 to 7, wherein $R^1$ is a 3,4-dimethylphenyl group, a tautomer, prodrug or pharmaceutically acceptable salt of the compound or a solvate thereof.
11. A thrombopoietin receptor activator containing the compound according to any one of 1 to 10, a tautomer, prodrug or pharmaceutically acceptable salt of the compound or a solvate thereof, as an active ingredient.
12. A preventive, therapeutic or improving agent for diseases against which activation of the thrombopoietin receptor is effective, which contains the thrombopoietin receptor activator according to 11, as an active ingredient.
13. A platelet increasing agent containing the thrombopoietin receptor activator according to 11, as an active ingredient.
14. Medicament containing the compound according to any one of 1 to 10, a tautomer, prodrug or pharmaceutically acceptable salt of the compound or a solvate thereof, as an active ingredient.

EFFECTS OF THE INVENTION

The pyrazole compounds of the present invention have affinity for and agonistic action on the thrombopoietin receptor and show potent platelet increasing action through stimulation of differentiation and proliferation of megakaryocytic progenitor cells and megakaryocytes.

The pyrazole compounds of the present invention are easily absorbable from the gastrointestinal tract and highly stimulate formation of megakaryocyte colonies. The orally absorbable pyrazole compounds are retained in blood at high levels and therefore useful especially as oral medicines.

Though patent document 26 discloses compounds having platelet increasing action, it does not disclose the pyrazole compounds of the present invention specifically enough to predict the especially excellent oral absorbability and the excellent megakaryocyte colony stimulating activity of the pyrazole compounds of the present invention.

Therefore, the pyrazole compounds of the present invention are useful as medicines and used as preventive, therapeutic and improving agents for diseases against which activation of the thrombopoietin receptor is effective, especially as platelet increasing agents.

BEST MODE FOR CARRYING OUT THE INVENTION

Now, the present invention will be described in detail.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Me" denotes methyl, "Et" denotes ethyl, "Pr" denotes propyl, and "Bu" denotes butyl.

First, the terms in the respective substituents $R^1$ to $R^6$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned. A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-3}$ alkoxy group may be a linear, branched or $C_3$ cycloalkoxy group, and methoxy, ethoxy, n-propoxy, i-propoxy, c-propoxy and the like may be mentioned.

Specific preferred examples of the substituent $R^1$ are phenyl groups substituted with one or more of the following substituents.

Substituents: a $C_{1-6}$ alkyl group, a $C_{1-3}$ alkyl group (the $C_{1-3}$ alkyl group is substituted with one or more halogen atoms) and a halogen atom.

Particularly preferred examples of the substituent $R^1$ are a 3,4-dimethylphenyl group, a 4-trifluoromethylphenyl group and a 3,4-dichlorophenyl group.

Specific preferred examples of the substituent $R^2$ are a hydrogen atom, a methyl group, an ethyl group, an i-propyl group, a n-propyl group and a trifluoromethyl group.

A particularly preferred example of the substituent $R^2$ is a methyl group.

Specific preferred examples of the substituent $R^3$ are thienyl groups substituted with one or more of the following substituents.

Substituent: (C=O)$NR^5R^6$ (wherein $R^5$ is a hydrogen atom or a $C_{1-3}$ alkyl group (the $C_{1-3}$ alkyl group may be substituted with one or more halogen atoms), and $R^6$ is a $C_{1-6}$ alkyl group (the $C_{1-6}$ alkyl group may be substituted with one or more halogen atoms, one or more hydroxyl groups, one or more $C_{1-3}$ alkoxy groups (the $C_{1-3}$ alkoxy groups may be substituted with one or more halogen atoms), one or more phenyl groups, one or more thienyl groups, one or more furyl groups or one or more pyridyl groups)))

A particularly preferred example of the substituent $R^3$ is represented by the formula (II):

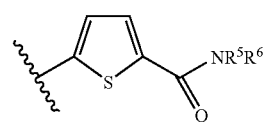

(II)

(wherein $R^5$ is a hydrogen atom, a methyl group or an ethyl group, and $R^6$ is a $C_{1-3}$ alkyl group (the $C_{1-3}$ alkyl group may be substituted with one or more 2-pyridyl groups)).

Another particularly preferred example of the substituent $R^3$ is represented by the formula (II):

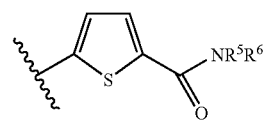

(II)

(wherein $R^5$ is a hydrogen atom, and $R^6$ is a $C_{1-3}$ alkyl group (the $C_{1-3}$ alkyl group may be substituted with one or more 4-pyridyl groups or $C_{1-3}$ alkoxy groups)).

Still another particularly preferred example of the substituent $R^3$ is represented by the formula (II) (wherein $R^5$ is a hydrogen atom, and $R^6$ is a methyl group substituted with a 2-pyridyl group).

Still another particularly preferred example of the substituent $R^3$ is represented by the formula (II):

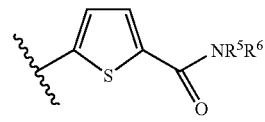

(II)

(wherein $R^5$ is a hydrogen atom, and $R^6$ is an i-propyl group, a methyl group substituted with a 4-pyridyl group or a 2-methoxyethyl group).

Still another particularly preferred example of the substituent $R^3$ is represented by the formula (II) (wherein $R^5$ is an ethyl group, and $R^6$ is an ethyl group).

Specific preferred examples of the substituent $R^4$ are a methyl group, an ethyl group, an i-propyl group, a n-propyl group and a trifluoromethyl group.

A particularly preferred example of the substituent $R^4$ is a methyl group.

Favorable compounds for use in the thrombopoietin receptor activator, the preventive, therapeutic or improving agent for diseases against which activation of the thrombopoietin receptor is effective and the platelet increasing agent of the present invention are as follows.

1) Compounds represented by the formula (I) wherein $R^2$ and $R^4$ are methyl groups, tautomers, prodrugs or pharmaceutically acceptable salts of the compounds or solvates thereof.

2) The compounds according to 1), wherein $R^1$ is a 3,4-dimethylphenyl group, tautomers, prodrugs or pharmaceutically acceptable salts of the compounds or solvates thereof.

3) The compounds according to 1), wherein $R^1$ is a 4-trifluoromethylphenyl group, tautomers, prodrugs or pharmaceutically acceptable salts of the compounds or solvates thereof.

4) The compounds according to 1), wherein $R^1$ is a 3,4-dichlorophenyl group, tautomers, prodrugs or pharmaceutically acceptable salts of the compounds or solvates thereof.

5) The compounds according to any one of 2) to 4), wherein $R^3$ is represented by the formula (II):

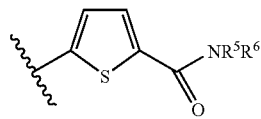

(wherein $R^5$ is a hydrogen atom or a $C_{1-3}$ alkyl group, and $R^6$ is a $C_{1-3}$ alkyl group (the $C_{1-3}$ alkyl group is substituted with a 2-pyridyl group)), tautomers, prodrugs or pharmaceutically acceptable salts of the compounds or solvates thereof.

6) The compounds according to any one of 2) to 4), wherein $R^3$ is represented by the formula (II):

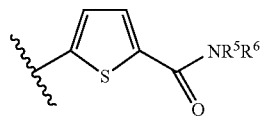

(wherein $R^5$ is a hydrogen atom or a $C_{1-3}$ alkyl group, and $R^6$ is a $C_{1-3}$ alkyl group (the $C_{1-3}$ alkyl group is substituted with a 4-pyridyl group or a $C_{1-3}$ alkoxy group)), tautomers, prodrugs or pharmaceutically acceptable salts of the compounds or solvates thereof.

7) The compounds according to any one of 2) to 4), wherein $R^3$ is represented by the formula (II):

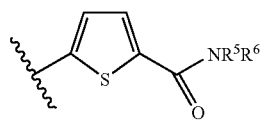

(wherein $R^5$ is a $C_{1-3}$ alkyl group, and $R^6$ is a $C_{1-6}$ alkyl group), tautomers, prodrugs or pharmaceutically acceptable salts of the compounds or solvates thereof.

8) The compounds according to any one of 2) to 4), wherein $R^3$ is represented by the formula (II):

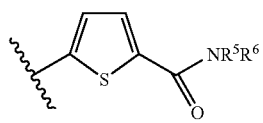

(wherein $R^5$ is a hydrogen atom, and $R^6$ is a $C_{1-3}$ alkyl group), tautomers, prodrugs or pharmaceutically acceptable salts of the compounds or solvates thereof.

9) The compounds wherein $R^4$ is a hydrogen atom, and $R^1$, $R^2$ and $R^3$ are any of the following combinations in Table 1, tautomers, prodrugs or pharmaceutically acceptable salts of the compounds or solvates thereof. The symbols in Table 1 denote the following substituents.

TABLE 1

| $R^1$ | $R^2$ | $R^3$ |
|---|---|---|
| Q1a | Me | Q3a |
| Q1a | Me | Q3b |
| Q1a | Me | Q3c |
| Q1a | Me | Q3d |
| Q1b | Me | Q3a |
| Q1b | Me | Q3b |
| Q1b | Me | Q3c |
| Q1b | Me | Q3d |
| Q1c | Me | Q3a |
| Q1c | Me | Q3b |
| Q1c | Me | Q3c |
| Q1c | Me | Q3d |
| Q1d | Me | Q3a |
| Q1d | Me | Q3b |
| Q1d | Me | Q3c |
| Q1d | Me | Q3d |
| Q1e | Me | Q3a |
| Q1e | Me | Q3b |
| Q1e | Me | Q3c |
| Q1e | Me | Q3d |
| Q1f | Me | Q3a |
| Q1f | Me | Q3b |
| Q1f | Me | Q3c |
| Q1f | Me | Q3d |

Q1a = 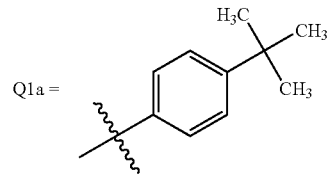

Q1b = 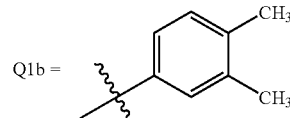

Q1c = 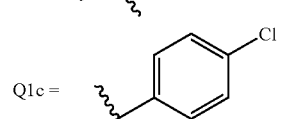

Q1d = 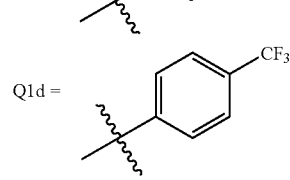

TABLE 1-continued

| | R¹ | R² | R³ |
|---|---|---|---|

Q1e = (3,4-dichlorophenyl)

Q1f = (4-bromophenyl)

Q3a = 5-[N-methyl-N-propyl-carbamoyl]thiophen-2-yl

Q3b = 5-[N,N-diethylcarbamoyl]thiophen-2-yl

Q3c = 5-[N-(pyridin-2-ylmethyl)carbamoyl]thiophen-2-yl

Q3d = 5-[N-methyl-N-(pyridin-2-ylmethyl)carbamoyl]thiophen-2-yl

10) The compounds wherein R⁴ is a methyl group, and R¹, R² and R³ are any of the following combinations in Table 2, tautomers, prodrugs or pharmaceutically acceptable salts of the compounds or solvates thereof. The symbols in Table 2 denote the following substituents.

TABLE 2

| R¹ | R² | R³ |
|---|---|---|
| Q1a | Me | Q3a |
| Q1a | Me | Q3b |
| Q1a | Me | Q3c |
| Q1a | Me | Q3d |
| Q1b | Me | Q3a |
| Q1b | Me | Q3b |
| Q1b | Me | Q3c |
| Q1b | Me | Q3d |
| Q1c | Me | Q3a |
| Q1c | Me | Q3b |
| Q1c | Me | Q3c |
| Q1c | Me | Q3d |
| Q1d | Me | Q3a |
| Q1d | Me | Q3b |
| Q1d | Me | Q3c |
| Q1d | Me | Q3d |
| Q1e | Me | Q3a |
| Q1e | Me | Q3b |
| Q1e | Me | Q3c |
| Q1e | Me | Q3d |

TABLE 2-continued

| R¹ | R² | R³ |
|---|---|---|
| Q1f | Me | Q3a |
| Q1f | Me | Q3b |
| Q1f | Me | Q3c |
| Q1f | Me | Q3d |

Q1a = (4-tert-butylphenyl)

Q1b = (3,4-dimethylphenyl)

Q1c = (4-chlorophenyl)

Q1d = (4-trifluoromethylphenyl)

Q1e = (3,4-dichlorophenyl)

Q1f = (4-bromophenyl)

Q3a = 5-[N-(2-methoxyethyl)carbamoyl]thiophen-2-yl

Q3b = 5-[N-(pyridin-4-ylmethyl)carbamoyl]thiophen-2-yl

Q3c = 5-[N-methyl-N-(pyridin-4-ylmethyl)carbamoyl]thiophen-2-yl

Q3d = 5-[N-isopropylcarbamoyl]thiophen-2-yl

11) The compounds according to 9) and 10), wherein R² is converted to a hydrogen atom, tautomers, prodrugs or pharmaceutically acceptable salts of the compounds or solvates thereof.

12) The compounds according to 9) and 10), wherein $R^2$ is converted to a trifluoromethyl group, tautomers, prodrugs or pharmaceutically acceptable salts of the compounds or solvates thereof.

13) The compounds according to 9) and 10), wherein $R^2$ is converted to an ethyl group, tautomers, prodrugs or pharmaceutically acceptable salts of the compounds or solvates thereof.

14) The compounds according to 9) and 10), wherein $R^2$ is converted to a n-propyl group, tautomers, prodrugs or pharmaceutically acceptable salts of the compounds or solvates thereof.

15) The compounds according to 9) and 10), wherein $R^2$ is converted to an i-propyl group, tautomers, prodrugs or pharmaceutically acceptable salts of the compounds or solvates thereof.

16) The compounds according to 9) and 15), wherein $R^4$ is converted to a trifluoromethyl group, tautomers, prodrugs or pharmaceutically acceptable salts of the compounds or solvates thereof.

17) The compounds according to 9) and 15), wherein $R^4$ is converted to an ethyl group, tautomers, prodrugs or pharmaceutically acceptable salts of the compounds or solvates thereof.

18) Thrombopoietin receptor activators containing the compounds according to 1) to 17), tautomers, prodrugs or pharmaceutically acceptable salts of the compounds or solvates thereof, as an active ingredient.

19) Preventive, therapeutic and improving agents for diseases against which activation of the thrombopoietin receptor is effective, which contain the thrombopoietin receptor activators according to 18), as an active ingredient.

20) Platelet increasing agents containing the thrombopoietin receptor activators according to 18), as an active ingredient.

21) Medicaments containing any of the compounds according to 1) to 17) or the compounds represented by the formula (I), tautomers, prodrugs or pharmaceutically acceptable salts of the activators or solvates thereof, as an active ingredient.

In the present invention, the compounds of the present invention represented by the formula (1) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —OCO(t-Bu), —$OCOC_{15}H_{31}$, —OCO(m-$CO_2$Na-Ph), —$OCOCH_2CH_2CO_2Na$, —$OCOCH(NH_2)$ $CH_3$, —$OCOCH_2N(CH_3)_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_{20}OCH_3$, —$NHCOCH(NH_2)CH_3$ and the like.

The preventive, therapeutic and improving agents for diseases against which activation of the thrombopoietin receptor is effective or platelet increasing agents which contain the thrombopoietin receptor activators of the present invention as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration for adults and about from 0.05 mg to 500 mg/human/day in the case of injections for adults, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (I) are prepared, for example, by the process represented by the formula (1) illustrated below.

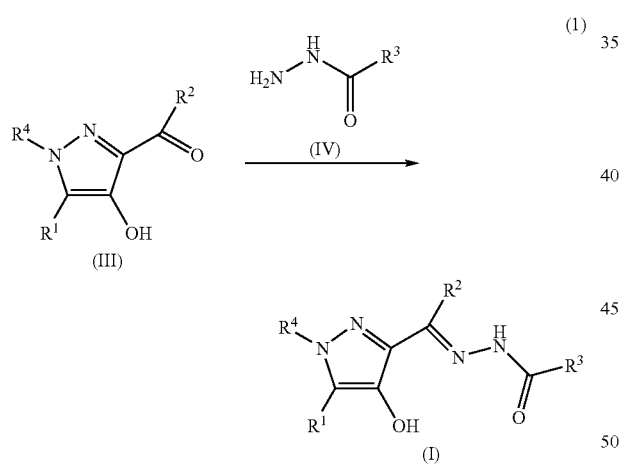

The reaction of the compound (III) with a —$NH_2$ compound (IV) in a solvent, if necessary in the presence of a catalyst, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

For the syntheses of the intermediates (III), the following method disclosed in J. Chem. Soc. Perkin. Trans. I, p. 81, (1985) may, for example, be referred to.

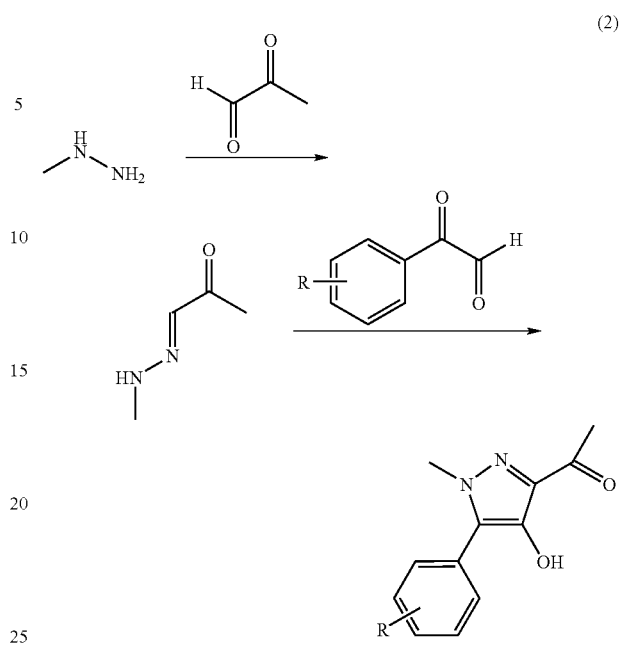

For synthesis of the —$NH_2$ compounds (IV), for example, the methods disclosed in Synthetic Commun., 28(7), 1223-1231 (1998), J. Chem. Soc., 1225 (1948) and J. Chem. Soc., 2831 (1952) may be referred to.

The compounds represented by the formula (I) can also be obtained by the process represented by the formula (3) illustrated below.

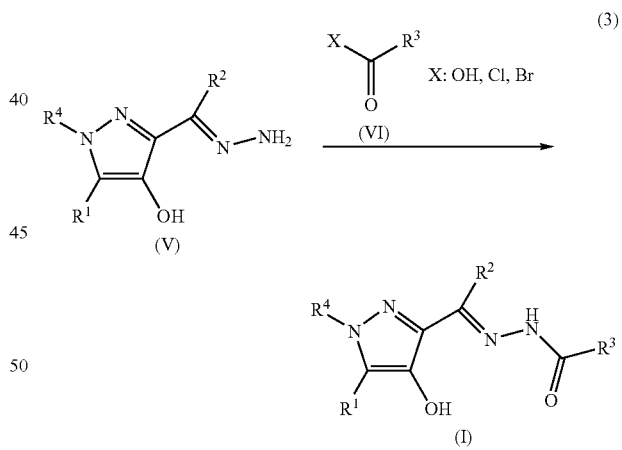

The reaction of the compound (V) with the compound (VI) in a solvent, if necessary, in the presence of a catalyst, a dehydrating condensation agent or a base, under heating with stirring gives a desired compound or its precursor. The precursor may be, if necessary, hydrolyzed, deprotected, reduced or oxidized to a desired compound. The compounds of the present invention usually can be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

The compound (VI) can be obtained by stirring the compound (III) with hydrazine or its equivalent in a solvent, if necessary in the presence of a catalyst, under heating.

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

LC/MS was measured under the following conditions.
LC/MS Condition 1
Column: Waters SunFire C18 (3.5 μm, 4.6×30 mm)
Eluent: acetonitrile/0.1% aqueous formic acid (10/90→30/70)
LC/MS Condition 2
Column: Waters SunFire C18 (3.5 μm, 4.6×30 mm)
Eluent: acetonitrile/0.1% aqueous formic acid (10/90→60/40)
LC/MS Conditions 3
Column: Waters Xterra MSC18 (5 μm, 4.6×50 mm)
Eluent: acetonitrile/0.1% aqueous formic acid (10/90→85/15)→
LC/MS Conditions 4
Column: Waters Xterra MSC18 (3.5 μm, 2.1×20 mm)
Eluent: acetonitrile/0.2% aqueous formic acid (20/80→90/10)

Reference Synthetic Example 1

Synthesis of
5-hydrazinocarbonylthiophene-2-carboxylic Acid Diethylamide

Methyl 5-(diethylcarbamoyl)thiophene-2-carboxylate (247 mg, 1.02 mmol) in ethanol (9 mL) was stirred with hydrazine monohydrate (495 mg, 10.2 mol) at 90° C. for 6 hours. After addition of water, the reaction solution was extracted with ethyl acetate and chloroform, and the extract was dried over anhydrous magnesium sulfate and concentrated to give the desired product (yield 89%).
Morphology: white solid
LC/MS: conditions 4 retention time 0.63 (min)
LC/MS (ESI$^+$) m/z; 242 [M+1]$^+$ Reference Synthetic Example 2

Synthesis of
5-hydrazinocarbonylthiophene-2-carboxylic Acid 2-picolylamide

The procedure in Reference Synthetic Example 1 was followed using methyl 5-(2-picolylcarbamoyl)thiopene-2-carboxylate to give the desired product (yield 81%).
Morphology: white solid
LC/MS: conditions 1 retention time 0.28 (min)
LC/MS (ESI$^+$) m/z; 277 [M+1]$^+$
LC/MS (ESI$^-$) m/z; 275 [M−1]$^-$ Reference Synthetic Example 3

Synthesis of
5-hydrazinocarbonylthiophene-2-carboxylic Acid 2-propylamide

Methyl 5-(2-propylcarbamoyl)thiophene-2-carboxylate (1.22 g, 5.37 mmol) in ethanol (40 mL) was heated with hydrazine monohydrate (2.7 g) at 85° C. for 16 hours with reflux. After cooling, the solvent was evaporated, the resulting solid was recrystallized from chloroform to give 549.2 mg of the desired product (yield 45%).
Morphology: colorless solid
LC/MS: conditions 2 retention time 1.07 (min)
LC/MS (ESI$^+$) m/z; 226 [M+1]$^+$ Reference Synthetic Example 4

Synthesis of
5-hydrazinocarbonylthiophene-2-carboxylic Acid 4-picolylamide

The procedure in Reference Synthetic Example 3 was followed using methyl 5-(4-picolylcarbamoyl)thiophene-2-carboxylate to give the desired product (yield 81%).
Morphology: white solid
LC/MS: conditions 1 retention time 0.23 (min)
LC/MS (ESI$^+$) m/z; 277[M+1]$^+$
LC/MS (ESI$^-$) m/z; 275 [M−1]$^-$ Reference Synthetic Example 5

Synthesis of
5-hydrazinocarbonylthiophene-2-carboxylic Acid 2-methoxyethylamide

The procedure in Reference Synthetic Example 3 was followed using methyl 5-(2-methoxyethylcarbamoyl)thiophene-2-carboxylate to give the desired product (yield 84%).
Morphology: white solid
LC/MS: conditions 1 retention time 0.34 (min)
LC/MS (ESI$^+$) m/z; 244 [M+1]$^+$
LC/MS (ESI$^-$) m/z; 242 [M−1]$^-$ Synthetic Example 1

Synthesis of 5-{1-[4-hydroxy-1-methyl-5-(4-trifluoromethylphenyl)-1H-pyrazol-3-yl]ethylidenehydrazinocarbonyl}thiophene-2-carboxylic Acid Diethylamide Potassium Salt 5-{1-[4-Hydroxy-1-methyl-5-(4-trifluoromethylphenyl)-1H-pyrazol-3-yl]ethylidenehydrazinocarbonyl}thiophene-2-carboxylic Acid Diethylamide (Free Form)

1-[4-Hydroxy-1-methyl-5-(4-trifluoromethylphenyl)-1H-pyrazol-3-yl]ethanone (28 mg, 0.10 mmol, synthesized in accordance with WO2004/108683), 5-hydrazinocarbonylthiophene-2-carboxylic acid diethylamide (24 mg, 0.10 mmol) prepared in Reference Synthetic Example 1 and p-toluenesulfonic acid (6 mg) were heated with 2-propanol (4 mL) for 14 hours with reflux. After cooling, the solvent was evaporated, and the resulting solid was recrystallized from 2-propanol-diethyl ether-n-hexane to give 27 mg of the desired product (yield 53%).
Morphology: pale yellow solid
LC/MS: conditions 3 retention time 3.44 (min)
LC/MS (ESI$^+$) m/z; 508 [M+1]$^+$
LC/MS (ESI$^-$) m/z; 506 [M−1]$^-$ 5-{1-[4-Hydroxy-1-methyl-5-(4-trifluoromethylphenyl)-1H-pyrazol-3-yl]ethylidenehydrazinocarbonyl}thiophene-2-carboxylic Acid Diethylamide Potassium Salt 5-{1-[4-Hydroxy-1-methyl-5-(4-trifluoromethylphenyl)-1H-pyrazol-3-yl]ethylidenehydrazinocarbonyl}thiophene-2-carboxylic acid diethylamide (13 mg, 0.025 mmol) was suspended in methanol (2.0 mL), and 0.1 M potassium hydroxide in methanol (0.25 mL) was added. The suspension was concentrated to dryness under reduced pressure to give the desired product (yield 95%).
Morphology: orange solid

Synthetic Example 2

Synthesis of 5-{1-[4-hydroxy-1-methyl-5-(4-trifluoromethylphenyl)-1H-pyrazol-3-yl]ethylidenehydrazinocarbonyl}thiophene-2-carboxylic Acid 2-picolylamide Potassium Salt 5-{1-[4-Hydroxy-1-methyl-5-(4-trifluoromethylphenyl)-1H-pyrazol-3-yl]ethylidenehydrazinocarbonyl}thiophene-2-carboxylic acid 2-picolylamide (free form)

1-[4-Hydroxy-1-methyl-5-(4-trifluoromethylphenyl)-1H-pyrazol-3-yl]ethanone (50 mg, 0.18 mmol) in dimethyl sulfoxide (1.0 mL) was heated with 5-hydrazinocarbonylthiophene-2-carboxylic acid 2-picolylamide (58 mg, 0.21 mmol) prepared in Reference Synthetic Example 2 at 110° C. for 21 hours. The solvent was evaporated, and the residue was washed with water and chloroform to give 79 mg of the desired product (yield 83%).
Morphology: pale yellow solid
LC/MS: conditions 2 retention time 3.27 (min)
LC/MS (ESI$^+$) m/z; 543 [M+1]$^+$
LC/MS (ESI$^-$) m/z; 541 [M−1]$^-$ 5-{1-[4-Hydroxy-1-methyl-5-(4-trifluoromethylphenyl)-1H-pyrazol-3-yl]ethylidenehydrazinocarbonyl}thiophene-2-carboxylic acid 2-picolylamide potassium salt The procedure in Synthetic Example 1 was followed using 5-{1-[4-hydroxy-1-methyl-5-(4-trifluoromethylphenyl)-1H-pyrazol-3-yl]ethylidenehydrazinocarbonyl}thiophene-2-carboxylic acid 2-picolylamide to give the desired product (yield is 100%).
Morphology: orange solid

Synthetic Example 3

Synthesis of 5-{1-[4-hydroxy-1-methyl-5-(4-trifluoromethylphenyl)-1H-pyrazol-3-yl]ethylidenehydrazinocarbonyl}thiophene-2-carboxylic Acid 2-propylamide 1-[4-Hydroxy-1-methyl-5-(4-trifluoromethylphenyl)-1H-pyrazol-3-yl]ethanone (50 mg, 0.18 mmol, synthesized in accordance with WO2004/108683), 5-hydrazinocarbonylthiophene-2-carboxylic acid 2-propylamide (40 mg, 0.18 mmol) prepared in Reference Synthetic Example 3 and p-toluenesulfonic acid (6 mg) were heated with 2-propanol (1.8 mL) for 14 hours with reflux. After cooling, the solvent was evaporated, and the resulting solid was washed with 2-propanol to give 36 mg of the desired product (yield 42%).

Morphology: pale yellow solid
LC/MS: conditions 2 retention time 3.92 (min)
LC/MS (ESI$^+$) m/z; 494 [M+1]$^+$
LC/MS (ESI$^-$) m/z; 492 [M−1]$^-$

Synthetic Example 4

Synthesis of 5-{1-[4-hydroxy-1-methyl-5-(4-trifluoromethylphenyl)-1H-pyrazol-3-yl]ethylidenehydrazinocarbonyl}thiophene-2-carboxylic Acid 4-picolylamide 1-[4-Hydroxy-1-methyl-5-(4-trifluoromethylphenyl)-1H-pyrazol-3-yl]ethanone (50 mg, 0.18 mmol) in dimethyl sulfoxide (0.88 mL) was heated with 5-hydrazinocarbonylthiophene-2-carboxylic acid 4-picolylamide prepared in Reference Synthetic Example 4 at 100° C. for 24 hours. The solvent was evaporated, and the residue was washed with water and chloroform to give 54 mg of the desired product (yield 56%).
Morphology: pale yellow solid
LC/MS: conditions 2 retention time 2.24, 2.67 (min)
LC/MS (ESI$^+$) m/z; 543 [M+1]$^+$
LC/MS (ESI$^-$) m/z; 541 [M−1]$^-$

Synthetic Example 5

Synthesis of 5-{1-[4-hydroxy-1-methyl-5-(4-trifluoromethylphenyl)-1H-pyrazol-3-yl]ethylidenehydrazinocarbonyl}thiophene-2-carboxylic Acid 2-methoxyethylamide To 1-[4-hydroxy-1-methyl-5-(4-trifluoromethylphenyl)-1H-pyrazol-3-yl]ethanone (50 mg, 0.18 mmol) and 5-hydrazinocarbonylthiophene-2-carboxylic acid 2-methoxyethylamide (64 mg, 0.26 mmol) prepared in Reference Synthetic Example 5 in dimethylformamide (0.88 mL), concentrated hydrochloric acid (15 µL, 0.18 mmol) was added at room temperature, and the resulting mixture was stirred for 15 hours. After the reaction, water was added, and the resulting crystals were recovered by filtration and dried. Chloroform was added, and the resulting crystals were recovered by filtration to give 59 mg of the desired product (yield 66%).
Morphology: yellow solid
LC/MS: conditions 2 retention time 3.68 (min)
LC/MS (ESI$^+$) m/z; 510 [M+1]$^+$
LC/MS (ESI$^-$) m/z; 508 [M−1]$^-$

Synthetic Example 6

Synthesis of 5-{1-[5-(3,4-dichlorophenyl)-4-hydroxy-1-methyl-1H-pyrazol-3-yl]ethylidenehydrazinocarbonyl}thiophene-2-carboxylic Acid 4-picolylamide 1-[5-(3,4-Dichlorophenyl)-4-hydroxy-1-methyl-1H-pyrazol-3-yl]ethanone (40 mg, 0.14 mmol) in dimethyl sulfoxide (1.0 mL) was mixed with 5-hydrazinocarbonylthiophene-2-carboxylic acid 4-picolylamide (39 mg, 0.14 mmol) prepared in Reference Synthetic Example 4 and left at 100° C. for 10.5 hours. The solvent was evaporated, and the residue was dissolved in chloroform (1.0 mL). After addition of n-hexane (2.0 mL), the resulting crystals were recovered by filtration to give 40 mg of the desired product (yield 53%).

Morphology: pale yellow solid

LC/MS: conditions 2 retention time 2.80 (min)

LC/MS (ESI$^+$) m/z; 543, 545 [M+1]$^+$

LC/MS (ESI$^-$) m/z; 541, 543 [M−1]$^-$

The structural formulae of the compounds obtained in the Reference Synthetic Examples and the Synthetic Examples are given below.

Reference Synthetic Ex. 1

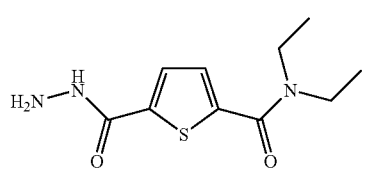

Reference Synthetic Ex. 2

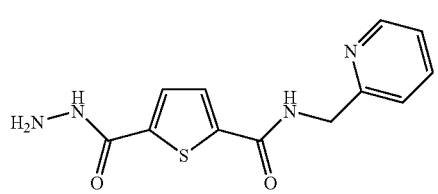

Reference Synthetic Ex. 3

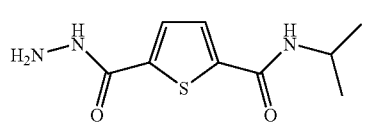

Reference Synthetic Ex. 4

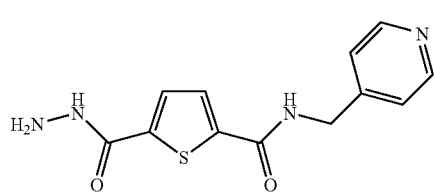

Reference Synthetic Ex. 5

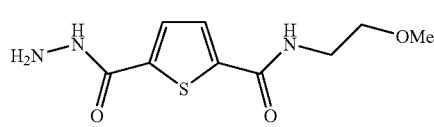

Reference Synthetic Ex. 6

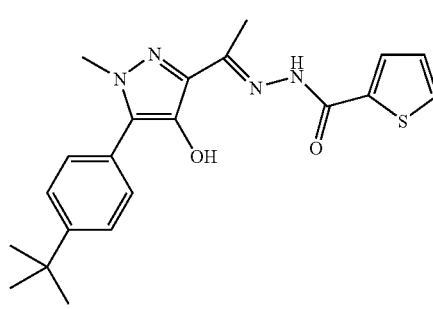

Patent document 26 Synthetic Ex. 34

Reference Synthetic Ex. 7

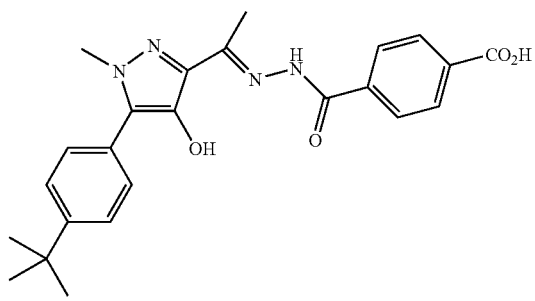

Patent document 26 Synthetic Ex. 3

Synthetic Ex. 1

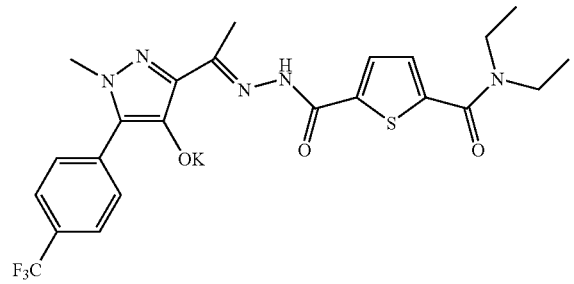

Synthetic Ex. 2

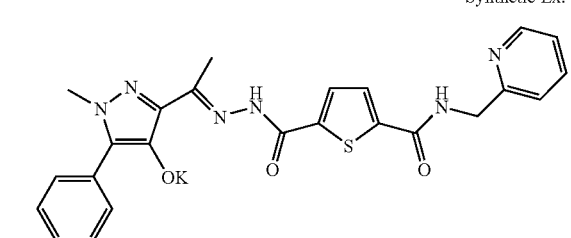

Synthetic Ex. 3

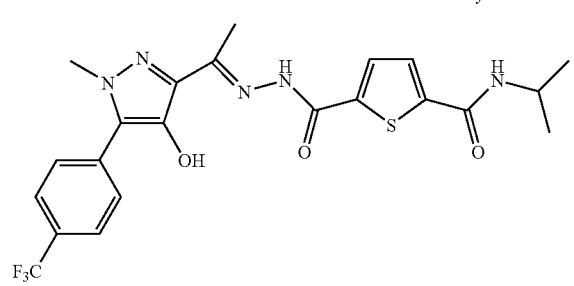

Synthetic Ex. 4

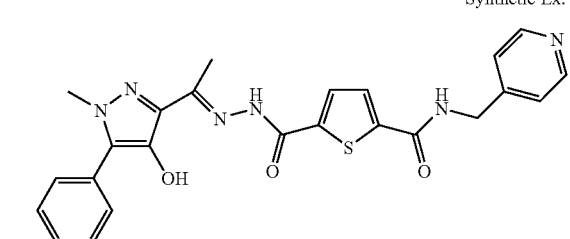

Synthetic Ex. 5

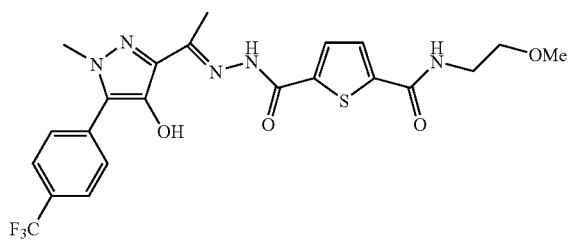

Synthetic Ex. 6

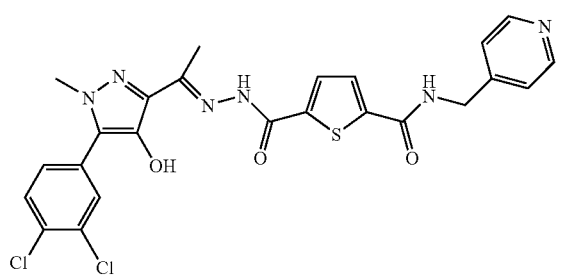

Assay Example 1

Stimulation of Proliferation of a Thrombopoietin-Dependent Cell Line

The reactivity of the compounds of the Synthetic Examples of the present invention with thrombopoietin (TPO) receptor was assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by thrombopoietin, while its mother cell line UT7/EPO exhibits no response to thrombopoietin. These two cell lines were subcultured in IMDM (GIBCO) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6 \times 10^4$ cells/mL. The cell suspension was transferred to a 96-well tissue culture plate (CORNING) in 100-μl aliquots. Then either thrombopoietin (Pepro Tech EC) or the compounds of the Synthetic Examples dissolved in dimethyl sulfoxide was diluted 83-fold with IMDM containing 10% fetal bovine serum and added to the aforementioned cell suspension in 20-μl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 h. The formazan pigment generated was detected by measuring the absorbance at 450 nm with a 96-well microplate reader (Nihon Molecular Devices, Spectramax 190). Proliferation of thrombopoietin-responsive UT7/EPO-mpl cells was stimulated by the compounds of the Synthetic Examples of the present invention in a concentration-dependent manner, while no effect of the compounds of the Synthetic Examples on proliferation was observed with UT7/EPO, the mother cell line. These results indicate that the compounds of the Synthetic Examples of the present invention act on the thrombopoietin receptor selectively as its activators.

The compounds of Synthetic Examples 1 to 6 (the compounds of Synthetic Examples 1 and 2 were tested in the free forms) were tested to determine the concentration of each compound that yields a growth rate corresponding to 50% of the growth of human leukemic cell line UT7/EPO-mpl observed in the presence of 10 ng/ml TPO ($EC_{50}$). The compounds of Synthetic Examples 1 to 6 all had $EC_{50}$ of about 10 ng/mL or below.

Assay Example 2

Each of the compounds of Synthetic Examples was suspended in a 99/1 liquid mixture of 0.5% methylcellulose/Polyoxyethylene Sorbitan Monooleate and orally administered to 7-week-old male Sprague-Dawley rats (Japan SLC, Inc.) at a dose of 10 mg/kg/10 mL through a stomach tube. Between 0.5 and 2 hours after the administration of the compounds, blood was periodically collected from the cervical vein with heparin as the anticoagulant. The blood was centrifuged at 3500 $min^{-1}$ for 10 minutes to obtain plasma. The plasma was added to the assay system used for assay of proliferation of a thrombopoietin-dependent cell line UT7/EPO-mpl in Assay Example 1 at final concentrations of from 0.1 to 3%, and the cell proliferation was assayed. The concentration of each compound in plasma was calculated from the cell proliferation in the presence of plasma by comparison with a standard curve of cell proliferation versus compound concentration prepared for each compound. The maximum concentration ($C_{max}$) of each of the compounds of Synthetic Examples in blood between 0.5 and 2 hours after the oral administration to rats is shown in Table 3.

TABLE 3

| Synthetic Example No. | Cmax (μg/mL) |
|---|---|
| 1 | 0.76 |
| 2 | 1.2 |

Assay Example 3

Megakaryocyte Colony Stimulating Activity

The action of the compounds of Synthetic Examples 2 to 6 of the present invention and Reference Synthetic Examples 6 to 7 on the proliferation, differentiation and maturation of megakaryocyte cells was measured by the megakaryocyte colony forming method using human bone marrow cells. Human bone marrow $CD34^+$ cells (Cambrex Bio Science Walkersville) were incubated on 2-well chamber slide for 11 days in a $CO_2$ incubator (5% $Co_2$, 37° C.) using Mega Cult™-C (StemCell Technologies) containing 0.1% (v/v) of the compounds of Synthetic Examples dissolved in dimethyl sulfoxide. After dehydration and fixation, the cells were stained with an anti-glycoprotein IIb/IIIa antibody in accordance with the instruction by the manufacturer. The colonies consisting of at least 8 stained megakaryocyte cells in each well were counted under a microscope. The megakaryocyte colony counts in at least 2 wells were averaged.

The results demonstrate that the compounds of the present invention have excellent megakaryocyte colony stimulating activity and increase platelets through the activity.

The results are shown in Table 4.

TABLE 4

| Compound | Colony count at 1 μg/mL |
|---|---|
| Synthetic Ex. 2 | 121 |
| Synthetic Ex. 3 | 141 |
| Synthetic Ex. 4 | 111 |
| Synthetic Ex. 5 | 335 |
| Synthetic Ex. 6 | 173 |
| Reference Synthetic Ex. 6 | 1 |
| Reference Synthetic Ex. 7 | 3 |

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The is granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| | |
|---|---|
| Compound represented by the formula (I) | 100 mg |
| Saturated Fatty Acid Glyceride | 1000 mL |

Solutions having the above-mentioned composition are usually administered to a patient intravenously at a rate of 1 mL per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The invention claimed is:
1. A compound represented by the formula (I):

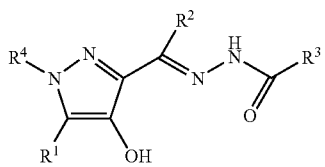

(I)

wherein
R$^1$ is a phenyl group which may be substituted with one or more C$_{1-6}$ alkyl groups, one or more C$_{1-3}$ alkyl groups substituted with one or more halogen atoms, or one or more halogen atoms;
R$^2$ is a hydrogen atom or a C$_{1-3}$ alkyl group which may be substituted with one or more halogen atoms;
R$^3$ is a thienyl group substituted with (C=O)NR$^5$R$^6$ wherein R$^5$ is a hydrogen atom or a C$_{1-3}$ alkyl group which may be substituted with one or more halogen atoms, and R$^6$ is a C$_{1-6}$ alkyl group which may be substituted with one or more halogen atoms, one or more hydroxyl groups, one or more C$_{1-3}$ alkoxy groups which may be substituted with one or more halogen atoms, one or more phenyl groups, one or more thienyl groups, one or more furyl groups or one or more pyridyl groups; and
R$^4$ is a C$_{1-3}$ alkyl group which may be substituted with one or more halogen atoms;
a tautomer or pharmaceutically acceptable salt of the compound or a solvate thereof.

2. The compound according to claim 1, wherein R$^2$ and R$^4$ are methyl groups, a tautomer or pharmaceutically acceptable salt of the compound or a solvate thereof.

3. The compound according to claim 2, wherein R$^1$ is a 3,4-dimethylphenyl group, a 4-trifluoromethylphenyl group or a 3,4-dichlorophenyl group, a tautomer or pharmaceutically acceptable salt of the compound or a solvate thereof.

4. The compound according to claim 3, wherein R$^3$ is represented by the formula (II):

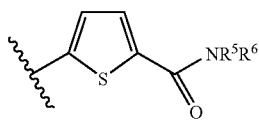

(II)

wherein
R$^5$ is a hydrogen atom or a C$_{1-3}$ alkyl group, and R$^6$ is a C$_{1-3}$ alkyl group which is substituted with a 2-pyridyl group,
a tautomer or pharmaceutically acceptable salt of the compound or a solvate thereof.

5. The compound according to claim 3, wherein R$^3$ is represented by the formula (II):

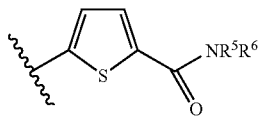

(II)

wherein
R$^5$ is a C$_{1-3}$ alkyl group, and R$^6$ is a C$_{1-6}$ alkyl group,
a tautomer or pharmaceutically acceptable salt of the compound or a solvate thereof.

6. The compound according to claim 3, wherein R$^3$ is represented by the formula (II):

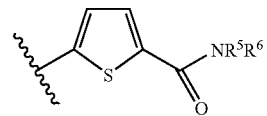

(II)

wherein
R$^5$ is a hydrogen atom or a C$_{1-3}$ alkyl group, and R$^6$ is a C$_{1-3}$ alkyl group which is substituted with a 4-pyridyl group or a C$_{1-3}$ alkoxy group,
a tautomer or pharmaceutically acceptable salt of the compound or a solvate thereof.

7. The compound according to claim 3, wherein R$^3$ is represented by the Formula (II):

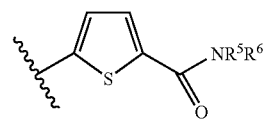

(II)

wherein
R$^5$ is a hydrogen atom, and R$^6$ is a C$_{1-3}$ alkyl group,
a tautomer or pharmaceutically acceptable salt of the compound or a solvate thereof.

8. The compound according to claim 4, wherein
R$^1$ is a 4-trifluoromethylphenyl group,
a tautomer or pharmaceutically acceptable salt of the compound or a solvate thereof.

9. The compound according to claim 4, wherein
R$^1$ is a 3,4-dichlorophenyl group,
a tautomer or pharmaceutically acceptable salt of the compound or a solvate thereof.

10. The compound according to claim 4, wherein
R$^1$ is a 3,4-dimethylphenyl group,
a tautomer or pharmaceutically acceptable salt of the compound or a solvate thereof.

11. The compound according to claim 5, wherein
R$^1$ is a 4-trifluoromethylphenyl group,
a tautomer or pharmaceutically acceptable salt of the compound or a solvate thereof.

12. The compound according to claim 5, wherein
R$^1$ is a 3,4-dichlorophenyl group,
a tautomer or pharmaceutically acceptable salt of the compound or a solvate thereof.

13. The compound according to claim 5, wherein
R$^1$ is a 3,4-dimethylphenyl group,
a tautomer or pharmaceutically acceptable salt of the compound or a solvate thereof.

14. The compound according to claim 6, wherein
R$^1$ is a 4-trifluoromethylphenyl group,
a tautomer or pharmaceutically acceptable salt of the compound or a solvate thereof.

15. The compound according to claim 6, wherein
R$^1$ is a 3,4-dichlorophenyl group,
a tautomer or pharmaceutically acceptable salt of the compound or a solvate thereof.

16. The compound according to claim 6, wherein
R$^1$ is a 3,4-dimethylphenyl group,
a tautomer or pharmaceutically acceptable salt of the compound or a solvate thereof.

17. The compound according to claim 7, wherein
R$^1$ is a 4-trifluoromethylphenyl group,
a tautomer or pharmaceutically acceptable salt of the compound or a solvate thereof.

18. The compound according to claim 7, wherein
R¹ is a 3,4-dichlorophenyl group,
a tautomer or pharmaceutically acceptable salt of the compound or a solvate thereof.

19. The compound according to claim 7, wherein
R¹ is a 3,4-trimethylphenyl group,
a tautomer or a pharmaceutically acceptable salt of the compound or a solvate thereof.

20. A method of treating thrombocytopenia in a patient in need thereof comprising administering to a patient an effective amount of the compound according to claim 1, a tautomer or pharmaceutically acceptable salt of the compound or a solvate thereof.

21. A method of therapeutically treating or improving diseases against which activation of the thrombopoietin receptor is effective, comprising administering a composition comprising the compound according to claim 1.

22. A method of increasing platelets, vascular endothelial cells and/or endothelial progenitor cells comprising administering to a patient in need thereof an effective amount of a composition comprising the compound according to claim 1.

23. A medicament comprising as an active ingredient the compound according to claim 1, a tautomer or pharmaceutically acceptable salt of the compound or a solvate thereof.

* * * * *